(12) United States Patent
Chen et al.

(10) Patent No.: US 7,890,282 B2
(45) Date of Patent: Feb. 15, 2011

(54) ESTIMATION OF CRYSTAL EFFICIENCY WITH AXIALLY COMPRESSED SINOGRAM

(75) Inventors: Mu Chen, Knoxville, TN (US); Vladimir Panin, Knoxville, TN (US); Michael E. Casey, Louisville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 218 days.

(21) Appl. No.: 12/212,457

(22) Filed: Sep. 17, 2008

(65) Prior Publication Data

US 2009/0072131 A1    Mar. 19, 2009

Related U.S. Application Data

(60) Provisional application No. 60/973,069, filed on Sep. 17, 2007.

(51) Int. Cl.
  *G01D 18/00*    (2006.01)
(52) U.S. Cl. .................... 702/104; 702/85; 250/363.03; 250/363.09
(58) Field of Classification Search .................... 702/85; 250/363.03, 363.09
  See application file for complete search history.

(56) References Cited

U.S. PATENT DOCUMENTS

2007/0018108 A1*  1/2007  Kitamura ................ 250/363.02
2007/0090300 A1*  4/2007  Sibomana et al. ...... 250/370.09
2007/0176087 A1*  8/2007  Wang et al. .............. 250/252.1
2009/0087065 A1*  4/2009  DaSilva et al. .............. 382/131

OTHER PUBLICATIONS

T R Oakes, V Sossi and T J Ruth; Normalization for 3D Pet with a low-scatter planar source and measured geometric factors; 1998; Physics in Medicine and Biology, vol. 43, No. 4, p. 961-972.*

Nuyts, "Simultaneous Maximum a Posteriori Reconstruction of Attenuation and Activity Distributions from Emission Sinograms", IEEE Transactions on Medical Imaging vol. 18, No. 5, May 1999.*

* cited by examiner

*Primary Examiner*—Jonathan C. Teixeira Moffat
(74) *Attorney, Agent, or Firm*—Peter L. Kendall

(57) ABSTRACT

The present invention provides a method for estimating crystal efficiency in a PET detector that takes axial compression into account. It does so via an iterative methodology in which a μ-map is first generated and then is used to obtain a solution for the equation $$L(\varepsilon_i) = \sum_{n \in N} y_n \log \sum_{i,j \in span} g_{ij}\varepsilon_i\varepsilon_j x_{ij} - \sum_{i,j \in span} g_{ij}\varepsilon_i\varepsilon_j x_{ij},$$

wherein $g_{ij}$ is a geometric factor for LOR(i,j), $\varepsilon_i$ and $\varepsilon_j$ are the efficiencies for crystal i and crystal j, and $x_{ij}$ is the line integral of the source distribution along LOR(i,j). Once efficiencies are determined, they are used to calibrate the PET detector.

5 Claims, 4 Drawing Sheets please
ENTER
/jtm/
12/1/2010

ESTIMATION OF CRYSTAL EFFICIENCY WITH AXIALLY COMPRESSED SINOGRAM

CROSS-REFERENCE TO RELATED APPLICATIONS

The present application is based on and claims priority benefit under 35 U.S.C. §119(e) of provisional application 60/973,069 filed Sep. 17, 2007, the contents of which are incorporated by reference.

TECHNICAL FIELD

In general, the present invention relates to nuclear medical imaging. More particularly, the invention relates to Positron Emission Tomography (PET) imaging and accurate estimation of scintillation crystal efficiency of PET detector blocks in a PET system.

GENERAL BACKGROUND OF THE INVENTION

Nuclear medicine is a unique specialty wherein radiation emission is used to acquire images which show the function and physiology of organs, bones or tissues of the body. The technique of acquiring nuclear medicine images entails first introducing radiopharmaceuticals into the body—either by injection or ingestion. These radiopharmaceuticals are attracted to specific organs, bones, or tissues of interest. Upon arriving at their specified area of interest, the radiopharmaceuticals produce gamma photon emissions which emanate from the body and are then captured by a scintillation crystal. The interaction of the gamma photons with the scintillation crystal produces flashes of light which are referred to as "events." Events are detected by an array of photo detectors (such as photomultiplier tubes), and their spatial locations or positions are then calculated and stored. In this way, an image of the organ or tissue under study is created from detection of the distribution of the radioisotopes in the body.

One particular nuclear medicine imaging technique is known as positron emission tomography, or PET. PET is used to produce images for diagnosing the biochemistry or physiology of a specific organ, tumor or other metabolically active site. The measurement of tissue concentration using a positron emitting radionuclide is based on coincidence detection of the two gamma photons arising from a positron annihilation. When a positron is annihilated by an electron, two 511 keV gamma photons are simultaneously produced and travel in approximately opposite directions. Gamma photons produced by an annihilation event can be detected by a pair of oppositely disposed radiation detectors capable of producing a signal in response to the interaction of the gamma photons with a scintillation crystal. Annihilation events are typically identified by a time coincidence between the detection of the two 511 keV gamma photons in the two oppositely disposed detectors; i.e., the gamma photon emissions are detected virtually simultaneously by each detector. When two oppositely disposed gamma photons each strike an oppositely disposed detector to produce a time coincidence event, they also identify a line-of-response (LOR) along which the annihilation event has occurred. An example of a PET method and apparatus is described in U.S. Pat. No. 6,858,847, which patent is incorporated herein by reference in its entirety.

FIG. 1 is a graphic representation of a LOR. An annihilation event 140 occurring in imaged object mass 130 may emit two simultaneous gamma rays (not shown) traveling substantially 180° apart. The gamma rays may travel out of scanned mass 130 and may be detected by block detectors 110A and 110B, where the detection area of the block detector defines the minimum area or maximum resolution within which the position of an incident gamma ray may be determined. Since block detectors 110A and 110B are unable to determine precisely where the gamma rays were detected within this finite area, the LOR 120 connecting block detectors 110A and 110B may actually be a tube with its radius equal to the radius of block detectors 110A and 110B. Similar spatial resolution constraints are applicable to other types of detectors, such as photomultiplier tubes.

To minimize data storage requirements, clinical projection data are axially compressed to within a predetermined span. With a cylindrical scanner, which has translational symmetry, the geometrical blurring resulting from axial compression may be modeled by projecting a blurred image into LOR space, followed by axial compression. This eliminates the storage of the axial components, and special algorithms have been developed to incorporate system response. The system response modeling then will allow the use of standard reconstruction algorithms such as Joseph's Method, and a reduction of data storage requirements.

The LOR defined by the coincidence events are used to reconstruct a three-dimensional distribution of the positron-emitting radionuclide within the patient. In two-dimensional PET, each 2D transverse section or "slice" of the radionuclide distribution is reconstructed independently of adjacent sections. In fully three-dimensional PET, the data are sorted into sets of LOR, where each set is parallel to a particular detector angle, and therefore represents a two dimensional parallel projection p(s, φ) of the three dimensional radionuclide distribution within the patient, where "s" corresponds to the displacement of the imaging plane perpendicular to the scanner axis from the center of the gantry, and "φ" corresponds to the angle of the detector plane with respect to the x axis in (x, y) coordinate space (in other words, φ corresponds to a particular LOR direction).

Coincidence events are integrated or collected for each LOR and stored in a sinogram. In this format, a single fixed point in f(x, y) traces a sinusoid in the sinogram. In each sinogram, there is one row containing the LOR for a particular azimuthal angle φ; each such row corresponds to a one-dimensional parallel projection of the tracer distribution at a different coordinate along the scanner axis. This is shown conceptually in FIG. 2.

It is known that the efficiency of the crystals in the detector modules or blocks of a PET scanner will vary from crystal to crystal in terms of luminescence per gamma strike. Therefore, it is important to estimate accurately the crystal efficiency of each detector in order to obtain good normalization for 3D PET data. Inaccurate knowledge of crystal efficiency can lead to artifacts, higher noise in the image, and/or poor uniformity in the reconstructed image.

One current approach utilizes the fan-sum method on acquired uniform cylinder sinogram data to estimate the crystal efficiency. However, in 3D acquisition mode with axial compression, each slice of the sinogram is the sum of multiple axial lines of response. If all crystal detectors have approximately the same efficiencies, this method can yield acceptable accuracy by ignoring the axial compression and assuming the direct planes are coincidences of a single crystal ring only. Where, however, there are weaker (i.e. less efficient) detector blocks in a PET system, this approach yields a blurred estimation of crystal efficiency.

Accordingly, there is a need in the art for a method for estimating crystal efficiency that takes axial compression into account. The present invention satisfies that need via an iterative methodology.

SUMMARY OF THE INVENTION

Thus, in one aspect, the invention provides a method for calibrating a PET detector having a plurality of detector crystal blocks or modules. According to the method, a μ-map is used as a calibration phantom. Subsequently, a solution is obtained for the equation:

$$L(\varepsilon_i) = \sum_{n \in N} y_n \log \sum_{i,j \in span} g_{ij}\varepsilon_i\varepsilon_j x_{ij} - \sum_{i,j \in span} g_{ij}\varepsilon_i\varepsilon_j x_{ij},$$

wherein $g_{ij}$ is a geometric factor for LOR(i,j), $\varepsilon_i$ and $\varepsilon_j$ are the efficiencies for crystal i and crystal j, and $x_{ij}$ is the line integral of the source distribution along LOR(i,j). In determining the solution, the μ-map is also used as a source distribution in calculating the line integral $x_{ij}$. The efficiency information is then used to calibrate a given PET detector in known fashion.

According to preferred embodiments, the p-map may be obtained using a CT scan of the calibration phantom, or it may be obtained mathematically using an emission sinogram of the calibration phantom. Furthermore, the line integral $x_{ij}$ may be calculated by forward projecting the source volume onto span 1 sinogram space. Still further, a conjugate gradient method may be used to obtain a solution to equation (1).

BRIEF DESCRIPTION OF THE DRAWINGS

The invention will now be described in greater detail in the following by way of example only and with reference to the attached drawings, in which.

DETAILED DESCRIPTION OF THE INVENTION

The present invention enables one to accurately model the contribution to the sinogram bins from each line of response (LOR). To do so, the method utilizes an attenuation correction file generated either from a CT scan or mathematically from an emission sinogram generated using a phantom and iteratively estimates individual crystal efficiency.

Figure 1:
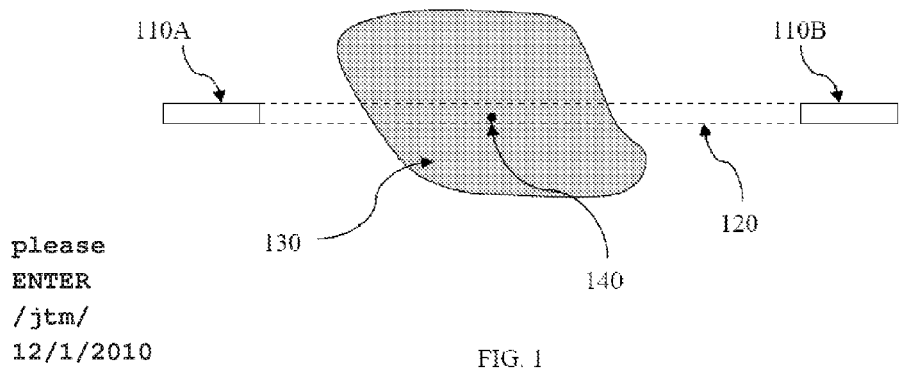
FIG. 1 shows a conceptual representation of a LOR in PET imaging.
Figure 2:
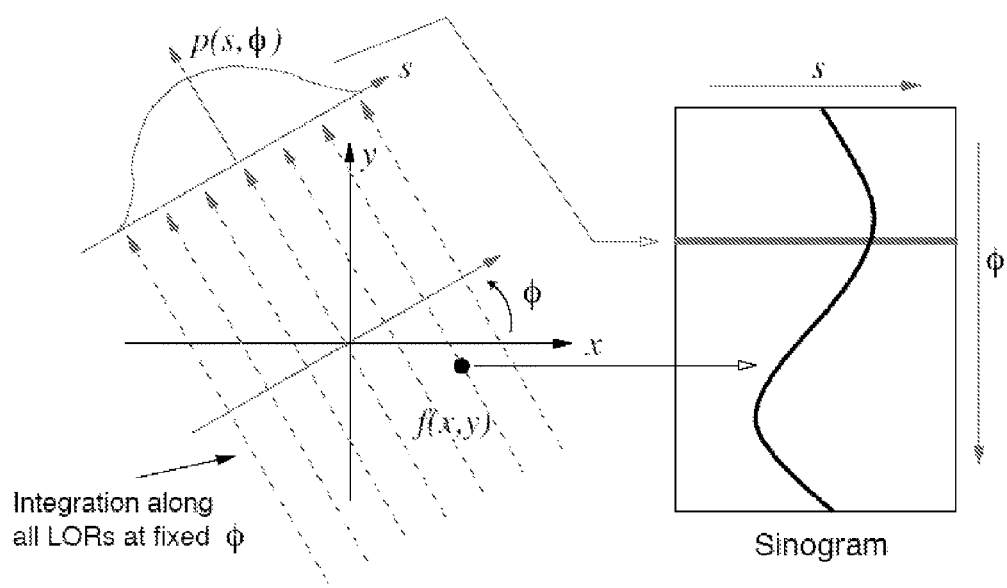
FIG. 2 is an illustration of the development of a sinogram.
Figure 3:
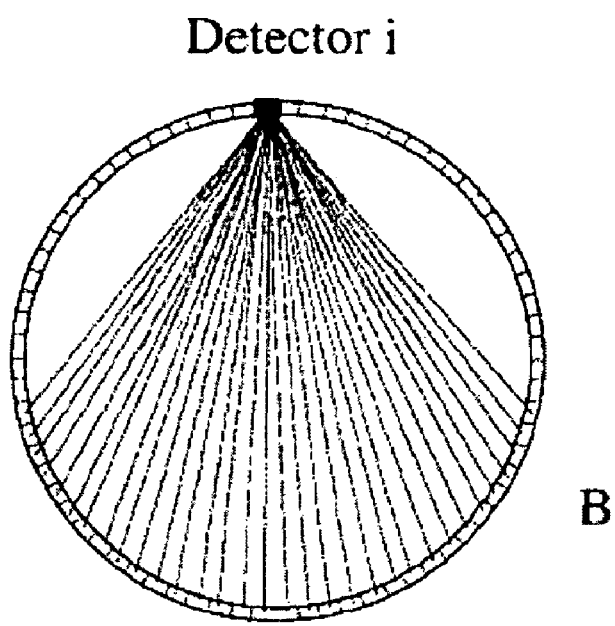
FIG. 3 is an illustration of fan-sum in LOR space.
Figure 4:
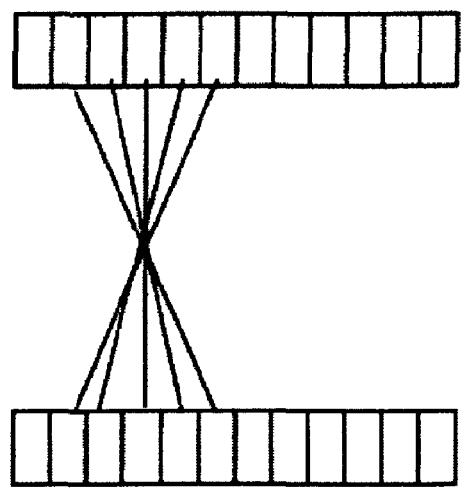
FIG. 4 is an illustration of an axially compressed sinogram.

The fan-sum method is applied on acquired uniform cylinder sinogram to estimate the crystal efficiency of each detector. LORs connecting one crystal i to the opposing group of crystals B are summed together to compute the efficiency of the crystal i, as illustrated in FIG. 3. Thus, in 3D acquisition mode with axial compression, each slice of the sinogram will be the sum of multiple axial lines of response, as illustrated in FIG. 4.

In the case where all crystal detectors have approximately the same efficiencies, acceptable accuracy can be achieved by ignoring the axial compression and assuming the direct planes are coincidences of a single crystal ring only. However, as noted above, if weaker detector blocks are present in the PET system, ignoring the axial compression would produce a blurred estimation of crystal efficiency and therefore an inaccurate normalization. Therefore, the present invention provides a calibration that takes axial compression into account.

The mean of the true (prompt-delay-scatter) detected events in LOR connecting detector i and detector j is $$\bar{y}_{ij} = g_{ij}\varepsilon_i\varepsilon_j x_{ij},$$

where $g_{ij}$ is the geometric factor for LOR(i,j), $\varepsilon_i$ and $\varepsilon_j$ are the efficiencies for crystal i and crystal j, and $x_{ij}$ is the line integral of the source distribution along LOR(i,j). In the case of a sinogram with axial span, $$\bar{y} = \sum_{i,j \in span} \bar{y}_{ij} = \sum_{i,j \in span} g_{i,j}\varepsilon_i\varepsilon_j x_{ij}.$$

Furthermore, the Poisson log likelihood for crystal efficiency is given as $$L(\varepsilon_i) = \sum_{n \in N} y_n \log \sum_{i,j \in span} g_{ij}\varepsilon_i\varepsilon_j x_{ij} - \sum_{i,j \in span} g_{ij}\varepsilon_i\varepsilon_j x_{ij}, \quad (1)$$

where N is the total number of axial sinograms receiving contribution from detector i. At this moment, geometric factor can be obtained through simulation, and dead time correction factor is ignored.

The line integral of the source distribution along LOR(i,j), $X_{ij}$, can be computed by forward projecting the source volume onto span 1 sinogram space. Assuming the source is uniformly distributed in the volume, μ-map obtained either from CT scans or mathematically from emission sinograms can be used as source distribution and in calculation of the line integral. The conjugate gradient method may be used to obtain a solution of crystal efficiency for equation (1) above, and the crystal efficiency information is then used to calibrate a given PET detector.

Figure 5:
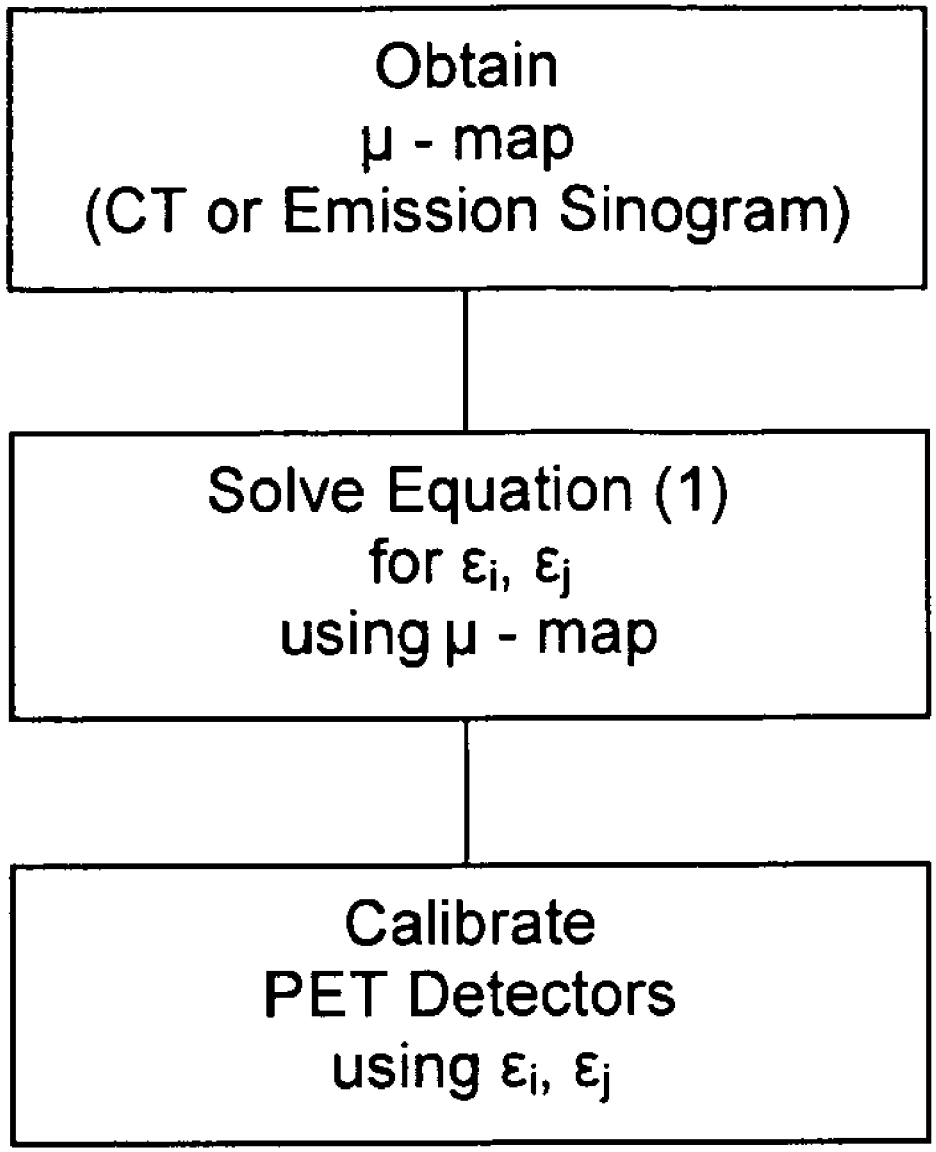
FIG. 5 is a flowchart illustrating the invention.

The method of the invention is illustrated in overview in FIG. 5. First, a μ-map is obtained (CT or Emission Sinogram). Next, equation (1) is solved for ϵi, ϵj using the μ-map. Finally, ϵi, ϵj are used to calibrate the PET system.

Figure 6:
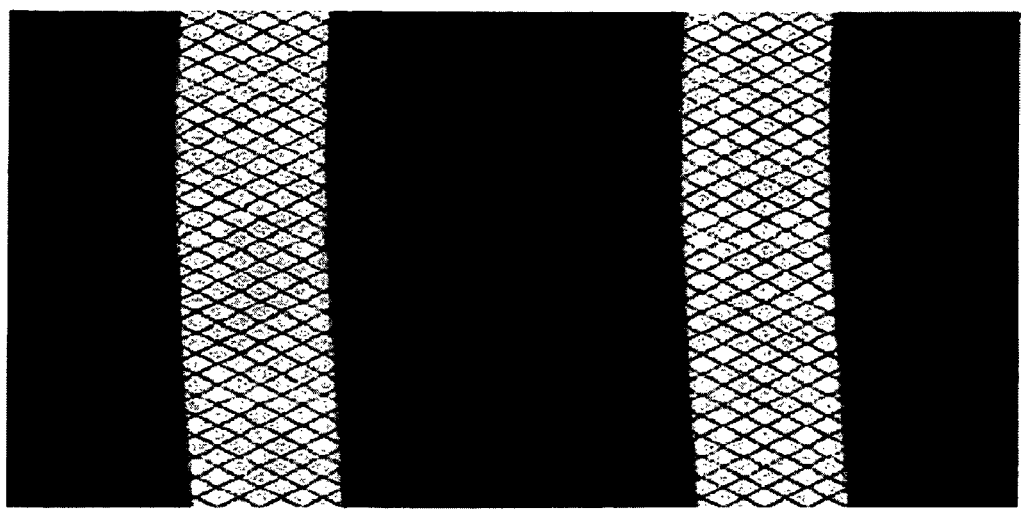
FIG. 6 is a comparison of normalized sinograms with (right hand side) and without (left hand side) modeling of axial compression.

Results: preliminary testing has been done to verify this method. In tests, geometric factors were ignored; source location was assumed to be in the center; and detector locations were computed with approximation. Results show that the estimation of the crystal efficiency is more accurate and the normalized sinogram has better uniformity, as illustrated in FIG. 6 (view on left hand side is without modeling axial compression; view on right hand side with modeling axial compression).

While the invention has been disclosed with reference to specific exemplary embodiments, modifications to and departures from the disclosed embodiments will occur to those having skill in the art. Accordingly, what is protected is defined solely by the scope of the following claims.

What is claimed is:

1. A method for calibrating a positron emission tomography (PET) detector having a plurality of detector crystals, comprising:

using a μ-map of said crystals as a calibration phantom;

computing, by a PET apparatus, a solution for the equation $$L(\varepsilon_i) = \sum_{n \in N} y_n \log \sum_{i,j \in span} g_{ij} \varepsilon_i \varepsilon_j x_{ij} - \sum_{i,j \in span} g_{ij} \varepsilon_i \varepsilon_j x_{ij},$$

wherein $g_{ij}$ is a geometric factor for line of response, LOR(i,j), $\epsilon_i$ and $\epsilon_j$ are the efficiencies for crystal i and crystal j, $y_n$ is the y-coordinate of an event, and $x_{ij}$ is the line integral of a source distribution along LOR(i,j), and wherein the μ-map is used as a source distribution in calculating the line integral $x_{ij}$; and calibrating the PET detector using $L(\epsilon_i)$.

2. The method of claim 1, wherein said μ-map is obtained using a CT scan.

3. The method of claim 1, wherein said μ-map is obtained mathematically using an emission sinogram of said calibration phantom.

4. The method of claim 1, wherein the line integral $x_{ij}$ is calculated by forward projecting the source volume onto span 1 sinogram space.

5. The method of claim 1, wherein a conjugate gradient method is used to obtain a solution to the equation in claim 1.

* * * * *